United States Patent
Bjarnsholt et al.

(10) Patent No.: US 10,603,289 B2
(45) Date of Patent: Mar. 31, 2020

(54) PROCESS FOR THE MANUFACTURE OF AJOENE DERIVATIVES

(71) Applicant: DANMARKS TEKNISKE UNIVERSITET, Lyngby (DK)

(72) Inventors: Thomas Bjarnsholt, Søborg (DK); Niels Høiby, Farum (DK); Peter Østrup Jensen, Copenhagen S (DK); Richard Phipps, Boston (GB); Meenakshi Sundaram Shanmugham, Copenhagen N (DK); Maria Alhede, Greve (DK); Louise Dahl Hultqvist, Kgs. Lyngby (DK); Tim Holm Jakobsen, Copenhagen S (DK); David Tanner, Copenhagen N (DK); Thomas Ostenfeld Larsen, Holte (DK); Michael Givskov, Humlebæk (DK)

(73) Assignee: DANMARKS TEKNISKE UNIVERSITET, Lyngby (DK)

( * ) Notice: Subject to any disclaimer, the term of this patent is extended or adjusted under 35 U.S.C. 154(b) by 0 days.

(21) Appl. No.: 15/980,471

(22) Filed: May 15, 2018

(65) Prior Publication Data

US 2018/0360773 A1  Dec. 20, 2018

Related U.S. Application Data

(63) Continuation of application No. 13/992,052, filed as application No. PCT/DK2011/050467 on Dec. 7, 2011, now abandoned.

(60) Provisional application No. 61/420,922, filed on Dec. 8, 2010.

(30) Foreign Application Priority Data

Dec. 8, 2010   (EP) .................................. 10194154

(51) Int. Cl.
| | | |
|---|---|---|
| *A61K 31/105* | (2006.01) | |
| *A61K 31/7036* | (2006.01) | |
| *A61K 45/06* | (2006.01) | |
| *C07C 319/22* | (2006.01) | |
| *A61M 16/06* | (2006.01) | |

(52) U.S. Cl.
CPC ........ *A61K 31/105* (2013.01); *A61K 31/7036* (2013.01); *A61K 45/06* (2013.01); *C07C 319/22* (2013.01); *A61M 16/0683* (2013.01); *Y02A 50/481* (2018.01)

(58) Field of Classification Search
None
See application file for complete search history.

(56) References Cited

U.S. PATENT DOCUMENTS

| 4,665,088 A | 5/1987 | Apitz-Castro et al. |
| 2007/0160725 A1 | 7/2007 | Lara-Cambil et al. |

FOREIGN PATENT DOCUMENTS

| EP | 0 185 324 A2 | 6/1986 |
| EP | 1 721 534 A1 | 11/2006 |
| WO | WO 99/21008 | 4/1999 |
| WO | WO 03/018082 A2 | 3/2003 |
| WO | WO 2010/100486 A2 | 9/2010 |

OTHER PUBLICATIONS

Ilić, Dusica P. et al, "Allicin and related compounds: biosynthesis, synthesis and pharmacological activity." Facta Universitatis (2011) 9(1) p. 9-20.*
Naganawa et al., "Inhibition of Microbial Growth by Ajoene, a Sulfur-Containing Compound Derived from Garlic," Applied and Environmental Microbiology, American Society for Microbiology, vol. 62, No. 11, Nov. 1996, pp. 4238-4242.
Bjarnsholt et al., "Garlic blocks quorum sensing and promotes rapid clearing of pulmonary Pseudomonas aeruginosa infections," SGM Journals, Microbiology, Aug. 18, 2005, pp. 3873-3880.
Block et al., "Antithrombotic Organosulfur Compounds from Garlic: Structural, Mechanistic, and Synthetic Studies," American Chemical Society, 1986, pp. 7045-7055.
Rasmussen et al., "Screening for Quorum-Sensing Inhibitors (QSI) by Use of a Novel Genetic System, the QSI Selector," Journal of Bacteriology, vol. 187, No. 5, Mar. 2005, pp. 1799-1814.
Apitz-Castro et al., "Ajoene, The Antiplatelet Principle of Garlic, Synergistically Potentiates and Antiaggregatory Action of Prostacyclin, Forskolin, Indomethacin and Dypiridamole on Human Platelets," Thrombosis Research, vol. 42, No. 3, Dec. 1, 1986, pp. 303-311.
Ratjen et al., "Aminoglycoside therapy against Pseudomonas aeruginosa in cystic fibrosis: A review," Journal of Cystic Fibrosis, European Cystic Fibrosis Society, Aug. 10, 2009, pp. 361-369.
Lawson et al., "Identification and HPLC Quantitation of the Sulfides and Dialk(en)yl Thiosulfinates in Commercial Garlic Products," Planta Med., 1991, pp. 363-370.
Brandt et al.,"DNA concentration and length in sputum of patients with cystic fibrosis during inhalation with recombinant human DNase," Thorax, 1995, 50, pp. 880-882.
Christensen et al.,"Molecular tools for study of biofilm physiology," Methods of Enzymology, 1999, 310, pp. 20-42.
Christensen et al.,"Impact of Pseudomonas aeruginosa quorum sensing on biofilm persistence in an in vivo intraperitoneal foreign-body infection model," Microbiology, 2007, 153, pp. 2312-2320.

(Continued)

*Primary Examiner* — Fred H Reynolds
(74) *Attorney, Agent, or Firm* — Pauley Erickson & Kottis (57) ABSTRACT

The present invention relates to the compound (E,Z)-ajoene of formula (1) for use in treatment of bacterial infections. Another aspect of the present invention is a composition comprising (E,Z)-ajoene of formula (1) and at least one antibiotic. Yet another aspect of the invention relates to a method for manufacturing (E,Z) ajoene of formula (1) wherein the conformation of the internal C=C— bond can be either E or Z or a mixture thereof, said method comprising reacting allicin of formula (3) with an acid in the presence of a solvent to provide (E,Z ajoene) of formula (1) as defined above. Yet another aspect of the invention is (E,Z)-ajoene of formula 1 obtainable by the method described above.

18 Claims, 8 Drawing Sheets

(56) References Cited

OTHER PUBLICATIONS

Fuqua et al.,"Quorum sensing in bacteria: the LuxR-LuxI family of cell density-responsive transcriptional regulators," Journal of Bacteriology, Jan. 1994, 176(2), pp. 269-275.
Mendelman et al.,"Aminoglycoside penetration, inactivation, and efficacy in cystic fibrosis sputum," The American Review of Respiratory Disease, Oct. 1985, 132(4), pp. 761-765.
Rahim et al.,"Cloning and functional characterization of the Pseudomonas aeruginosa rhlC gene that encodes rhamnosyltransferase 2, an enzyme responsible for di-rhamnolipid biosynthesis," Molecular Microbiology, 2001, 40(3), pp. 708-718.
Rasmussen et al.,Identity and effects of quorum-sensing inhibitors produced by *Penicillium* species, Microbiology, 2005, 151, pp. 1325-1340.
Waag et al.,"Allicin and derivatives are cysteine protease inhibitors with antiparasitic activity," Bioorganic & Medicinal Chemistry Letters, 2010, 20, pp. 5541-5543.
Wagner, Victoria E. et al.,"Microarray Analysis of Pseudomonas aeruginosa Quorum-Sensing Regulons: Effects of Growth Phase and Environment" Journal of Bacteriology, vol. 185, No. 7, Apr. 2003, pp. 2080-2095.
Katzen, Mollie, The Moosewood Cookbook (1977) ISBN 0-89815-490-1, p. 102 only.
Ankri, Serge and Mirelman, David;"Antimicrobial properties of allicin from garlic." Microbes and Infection (1999), 2, pp. 125-129.
Hudault, S. et al, "*Escherichia coli* strains colonising the gastrointestinal tract protect germ free mice against *Salmonella typhimurium* infection." Gut (2001), 49, pp. 47-55.
Walker, Travis S. et al.,"Pseudomonas aeruginosa—plant root interactions. Pathogenicity, biofilm formation, and root exudation." Plant Physiol. (2004), 134, pp. 320-331.
Bonaventura, Giovanni Di et al.,"Biofilm Formation by Stenotrophomonas maltophilia: Modulation by Ouinolones, Trimethoprim-Sulfamethoxazole, and Ceftazidime" Antimicrobial Agent and Chemotherapy, vol. 48, No. 1, Jan. 2004, pp. 151-160.
Fujino, Satoru et al.,"Three Cases of Stenotrophomonas maltophilia pneumonia" The Journal of the Japanese Respiratory Society, 2003, vol. 47, No. 7, 2003, pp. 463-468—Abstract.
Kalia, Vipin Chandra, "Quorum sensing inhibitors: an overview." Biotech. Adv. (2013), 31, pp. 224-245.
Anderson, Gregory G. et al.,"In vitor analysis of tobramycin treated pseudomonas aeruginosa biofilms on cystic fibrosis is derived airway epithelial cells." Infect. Immun. (2008) , 76(4), pp. 1423-1433.
Høiby et al.,"Antibiotic resistance of bacterial biofilms", International Journal of Antimicrobial Agents 35, 2010, pp. 322-332.
Mah et al.,"Mechanisms of biofilm resistance to antimicrobial agents", Trends in Microbiology, vol. 9, No. 1, Jan. 2001.

* cited by examiner

PROCESS FOR THE MANUFACTURE OF AJOENE DERIVATIVES

RELATED APPLICATIONS

This application is a continuation of U.S. patent application Ser. No. 13/992,052, filed Nov. 1, 2013, which is a 35 U.S.C. § 371 filing of International Patent Application No. PCT/DK2011/050467, filed Dec. 7, 2011, which claims priority to European Patent Application No. 10194154.0, filed Dec. 8, 2010, and U.S. Patent Application Ser. No. 61/420,922, filed Dec. 8, 2010. The entire contents of each of the above documents are incorporated herein by reference.

TECHNICAL FIELD OF THE INVENTION

The present invention relates to a chemical process the end product of which exhibits direct medical applications. The product of the chemical process known as ajoene has been found highly useful for the treatment of bacterial infections comprising biofilm forming bacteria by blocking expression of important quorum sensing controlled virulence factors. The invention also relates to a product obtainable by the above chemical process which shows synergistic antimicrobial effects with antibiotics. In particular the present invention relates to the synthesis of ajoene derivatives via an oxidation of diallyldisulphide to allicin which is subsequently treated with an acid to obtain ajoene E,Z isomers in a given ratio. Ajoene may be subjected to oxidation to obtain oxidized variations. Further aspects of the invention involve a composition of ajoene derivatives with an antibiotic and the use of ajoene derivatives for the treatment of bacterial infections comprising biofilm forming bacteria.

BACKGROUND OF THE INVENTION

Bacterial infections are an increasing problem worldwide. The widespread use of conventional antibiotics has provoked the development of increasingly resistant bacterial strains along with a depleting arsenal of sufficiently effective antibiotics.

As a result, research towards a deeper understanding of the mechanisms involved in bacterial infections is increasing. Thus, it has been discovered that a wide variety of bacteria coordinate their behaviour through cell-to-cell communication mediated by small, diffusible signals. This phenomenon has been dubbed quorum sensing (QS) [W. C. Fuqua et al., J. Bacteriol., 1994, 176, p 269-275], and is prevalent among bacteria that form complex surface attached communities called biofilms. It is estimated by the National Health Institute of America that 80% of persistent bacterial infections involve biofilms. QS enables bacteria to keep track of their numbers, and is considered to afford them a mechanism for minimizing host response by delaying the production of virulence factors until sufficient bacteria have been amassed to overwhelm host-defence mechanisms. Blocking of QS (either completely or partly) reinstates proper action of the host-defence system which subsequently eliminates bacterial intruders. Therefore, inhibition of QS presents an alternative therapeutic approach to the traditional antibiotic-mediated bacterial killing or growth inhibition.

It has been shown that garlic extract blocks QS and promotes rapid clearing of pulmonary infections caused by the bacterial strain *Pseudomonas aeruginosa* [T. Bjarnsholt et al., Microbiology, 2005, 151, p. 3873-3880]. *Pseudomonas aeruginosa* forms biofilm communities and utilizes QS through the production of signal molecules such as N-acyl homoserine lactones (AHL) and quinolones PQS). Garlic extract is also a well known natural medicine product having antibacterial and cholesterol lowering effects, among others.

Ajoene [(E,Z)-4,5,9-trithiadodeca-1,6,11-triene-9-oxide] has previously been shown to be an active ingredient in the antimicrobial garlic extracts along with allicin and other organosulfur derivatives. However, in a study on ajoene (the E:Z=1:4 isomer used), although a strong growth inhibitor of Gram positive bacteria, ajoene was shown to have a varied inhibitory effect on Gram negative bacteria, and no measurable growth inhibitory effect on *P. aeruginosa* [R. Naganawa et al., Applied and Environmental Microbiology, 62, 1996, p. 4238-4242].

Present processes for the manufacture of ajoene derivatives include the isolation of ajoene derivatives or precursors from garlic extract and various synthetic approaches. Isolation from garlic is highly tedious and inefficient as the amount of ajoene available pr. Kg raw garlic is minute i.e. in the range of 10 mg and HPLC separation from related compounds in garlic is a necessity. Some synthetic and semi-synthetic approaches to ajoene and various derivatives have been disclosed in the prior art. Eric Block and co-workers have disclosed a synthetic approach starting from an oxidation of diallyl disulphide or derivatives and subsequent heating of the resulting crude allicin or derivatives to form ajoene and derivatives [EP 185324 and Block et al., J. Am. Chem. Soc., 1986, 108, p. 7045-7055]. Apitz-Castro and co-workers have presented a semi-synthetic approach where allicin (allyl 2-propenethiosulfinate) is isolated from garlic bulbs and subsequently heated and treated with a lower alkyl alcohol to produce (E,Z)-ajoene derivatives [U.S. Pat. No. 4,665,088]. Recently a method of converting extracted allicin to ajoene using acetic acid in acetone was also reported, however crude impure starting material was used (i.e. crude allicin extracted from garlic) [WO 2010/100486]. However, the yields in the above methods have often been poor or purification by HPLC chromatography has been necessary leading to low yields of ajoene at high purification costs. Furthermore these synthetic approaches often lack control of the (E,Z)-isomeric outcome of the reaction, while still maintaining high yields.

Consequently, an alternative and improved method for the manufacture of ajoene derivatives would be advantageous.

It has now surprisingly been found that the synthesis of ajoene derivatives can be achieved in higher yields and better crude purities than previously obtained, while being able to vary the ratio of (E,Z) isomers in the final product via specific variations in the reaction conditions. Also, it was surprisingly found that certain mixtures of ajoene derivatives and/or isomers including those obtained by the above synthetic process and applying a single chromatographic purification step were effective QS inhibitors of biofilm forming bacteria, both when applied alone and in composition with conventional antibiotics.

SUMMARY OF THE INVENTION

Thus, an object of the present invention relates to providing a synthetic procedure for the effective production of ajoene derivatives or specific mixtures thereof which are applicable in the treatment of bacterial infections using QS inhibition.

In particular, it is an object of the present invention to provide a process for the manufacture of (E,Z)-ajoene [(E, Z)-4,5,9-trithiadodeca-1,6,11-triene-9-oxide] in controllable E:Z ratios that solves the above mentioned problems of the prior art with low product yields and time consuming and expensive purification procedures.

Thus, one aspect of the present invention is (E,Z)-ajoene of formula (1) for use in treatment of bacterial infections.

Another aspect of the present invention is a composition comprising (E,Z)-ajoene of formula (1) and at least one antibiotic.

Yet another aspect of the invention relates to a method for manufacturing (E,Z) ajoene of formula (1)

(1)

wherein the conformation of the internal —C=C— bond can be either E or Z or a mixture thereof, said method comprising reacting allicin of formula (3)

(3)

with an acid in the presence of a solvent to provide (E,Z ajoene) of formula (1) as defined above.

Yet another aspect of the invention is (E,Z)-ajoene of formula (1) obtainable by the method described above.

BRIEF DESCRIPTION OF THE FIGURES

FIG. 2 shows an exemplary scheme depicting the synthetic route towards further oxidized derivatives of ajoene. The reaction conditions were iii) 4 equivalents of peracetic acid in dichloromethane at 0° C. to room temperature for 12 h, 38% yield or 4 equivalents of DMDO in acetone at −10° C. for 6 h at 82% yield. iv) Potassium permanganate in acetone at −20° C. for 2 h at 96% yield. v) 2 equivalents of DMDO in acetone at −10° C. for 6 h giving 78% yield. vi) Lithiated sulphide (PhSLi) in THF at −78° C. to 0° C. for 1 h giving 86% yield.

The present invention will now be described in more detail in the following.

DETAILED DESCRIPTION OF THE INVENTION

Definitions

Prior to discussing the present invention in further details, the following terms and conventions will first be defined:

In the context of the present invention the term (E,Z)-ajoene derivatives or (E, Z)-isomers of ajoene derivatives refers to derivatives of ajoene which are either isolated as substantially pure E-ajoene derivatives, substantially pure Z-ajoene derivatives or as mixtures of E- and Z-ajoene derivatives. The (E,Z) designations refers to the internal —C=C— double bond of ajoene as shown in the structures by a wavy line where the configuration may vary. The term "derivatives" refers to both the two isomers (E) and (Z) and mixtures thereof and also to oxidized and/or reduced derivatives of (E,Z) ajoene and mixtures thereof.

An oxidizing agent, as defined herein, is any chemical reactant capable of changing the oxidation state of a molecule from its original oxidation state to a higher oxidation state. Similarly a reducing agent is any chemical reactant capable of changing the oxidation state of a molecule from its original oxidation state to a lower oxidation state.

In the context of the present invention an acid comprises both inorganic and organic acids. This includes organic acid anhydrides or any other pro-acids. As defined herein a pro-acid is any compound capable of converting into an acid under certain conditions. Such conditions could include heating or subjection to an aqueous environment. Any mixture of acids is also inferred.

As described herein biofilm refers to any aggregated, often but not necessarily a surface bound (sessile) community of bacteria embedded in a biopolymeric matrix showing increased resistance e.g. to antibiotics and important parts of the innate immune system, as compared to their planktonic counterparts.

In the context of the present invention the term quorum sensing (QS) refers to a bacterial behavioural coordination mechanism operating by means of cell-to-cell communication transmitted by low molecular weight, diffusible signal molecules. QS systems play an important role during the initial event of an infection. By employing three QS systems (denoted Las, Rhl and PQS) to control expression of its impressive arsenal of virulence factors many of which are antigenic determinants, certain bacteria such as *P. aeruginosa* is able to operate in a stealthy manner until a certain cell density is reached where the QS system is activated and virulence and immune protection is switched on. Upon activation of the QS system, a coordinated release of tissue damaging and immune defence degrading virulence factors takes place.

Also in the present context N-acyl-homoserine lactone producing bacteria is defined as bacteria utilising N-acyl-homoserine lactones as messenger molecules in their cell-to-cell communication during quorum sensing.

As defined herein a quorum sensing inhibitor or QS-inhibitor is a substance or mixture of substances capable of inhibiting bacterial QS based communication. Blockage of QS processes either by mutation in regulatory genes or by a QS inhibitor makes said bacteria more vulnerable to both conventional antibiotics, in particular aminoglycosides such as tobramycin and important components of the cellular host-defence such as PMN-leukocytes (PolyMorphoNuclear-leukocytes).

As mentioned above the first aspect of the present invention provides a method for making compounds of general formula (1)

(1)

also referred to as (E,Z)-ajoene. The conformation of the internal —C═C— bond can be either E or Z or a mixture thereof. The method comprises providing an intermediate compound of formula (3) also referred to as allicin (3)

and treating said compound of formula (3) with an acid in the presence of a solvent to provide compounds of formula (1) as defined above. In a preferred embodiment the concentration of the solution containing compound (3) may be 0.06-6.0 M, preferably 0.12-3.0 M, 0.24-1.5 M, 0.48-0.8 M, such as 0.6 M. The acid can be added in an excess or stoichiometric amount, but may typically be added in a catalytic amount such as 5-50 mol %, 10-40 mol %, 15-30 mol %, such as 20 mol %. In a preferred embodiment the acid added in the conversion of intermediate (3) to compounds of formula (1) may be a a number of acids, such as carboxylic acids including acetic acid, propionic acid, butyric acid, pentanoic acid, hexanoic acid, or triflouroacetic acid (TFA), or p-toluenesulfonic acid (TsOH), methanesulfonic acid (MsOH), camphorsulphonic acid (CSA). The preferred acid is acetic acid. The choice of acid has impact on the obtained ratio of E:Z isomers, i.e. the acid used and the corresponding E:Z ratio obtained may be for example triflouroacetic acid (E:Z=about 1:1), p-toluenesulfonic acid (E:Z=about 1:4), methanesulfonic acid (E:Z=about 1:4), and camphorsulphonic acid (E:Z=about 1:5), when using 40 V/V % aqueous acetone as the solvent.

In a preferred embodiment of the acid treatment providing the compound of formula (1), the solvent used is 10-70 V/V % aqueous acetone, preferably 20-60 V/V %, 30-50 V/V % such as 40 V/V % aqueous acetone (i.e. 60% acetone in 40% water). After addition of the acid the reaction temperature may be adjusted to be in the range of 0-100° C., preferably 20-80° C., such as 40-70° C., preferably 50-65° C., such as 64° C. The reaction time can be from 1-24 h, preferably 2-10 h, such as 3-5 h, preferably 4 h. The use of aqueous acetone as solvent provides the compounds of formula (1) in an E:Z ratio of 1:2-1:6, preferably 1:3-1:5, such as about 1:4, when using acetic acid in the acid treatment.

In yet another preferred embodiment of the methods described above providing the compound of formula (1), the solvent used during the acid treatment of intermediate (3) is toluene or aqueous benzene. The aqueous benzene can be 1-50 V/V % aqueous benzene, preferably 5-30 V/V %, such as 7-20 V/V %, preferably 10 V/V % aqueous benzene (i.e. 90% benzene in 10% water). After addition of the acid the reaction temperature may be adjusted to be in the range of 0-100° C., preferably 10-80° C., such as 20-60° C., preferably 30-50° C., such as 40° C. The reaction time for the acid treatment in toluene or aqueous benzene can be from 2-96 h, preferably 24-72 h, such as 36-60 h, preferably 48 h. The use of toluene or aqueous benzene as solvent provides the compounds of formula (1) in an E:Z ratio of 6:1-20:1, such as about 10:1, when using acetic acid in the acid treatment.

The purification of the obtained products may typically be performed using standard solvent extraction techniques followed by column chromatographic purification, but other methods may also be used such as distillation, preparative thin layer chromatography or crystallization for solid compounds.

In a preferred embodiment of the purification of compound (1) the reaction mixture is cooled to room temperature and diluted with 3 volumes of a 1:1 mixture of water and methanol followed by an extraction with an apolar solvent such as pentane. The aqueous fraction may be saturated with ammonium sulphate and further extracted with a more polar solvent than pentane such as dichloromethane. (E,Z)-ajoene (1) can be isolated by concentrating the combined organic extracts and subjecting the crude product to silica column chromatography using an eluent mobile phase comprising 40-99 V/V % ethyl acetate in pentane, preferably 50-90 V/V %, 60-80 V/V %, such as 70 V/V %.

The purity of (E,Z)-ajoene after the above procedure may be 95-99.5%, such as 97-99.5%, 98-99.5%, 99-99.5% such as about 99.5%. It was surprisingly found by the inventors, that upon further purification of the product obtained after column chromatography, e.g. using reverse phase HPLC chromatography, or other purification steps, said (E,Z)-ajoene product lost all or parts of its biological activity, in e.g. the assays as described in the examples. This was also found when isolating pure (E)-ajoene and/or pure (Z)-ajoene, e.g. using HPLC. It is speculated that small amounts of ajoene derived chemistry, i.e. compounds related to ajoene, such as less than 5%, 3%, 2%, 1%, such as less than 0.5% may be highly important in the stabilisation of (E,Z)-ajoene and derivatives, towards degradation, e.g. oxidation, reduction and or cleavage, both in vitro but importantly also in vivo.

One embodiment of the invention is a method as described above wherein the (E,Z)-ajoene of formula (1) is subjected to no more than one chromatographic purification step, said chromatographic purification step not comprising reversed phase HPLC.

After purification the (E,Z)-ajoene derivatives can be isolated as mixtures of isomers in yields based on compound (3) of at least 10 mol %, preferably 15 mol %, 20 mol %, 25 mol %, such as at least 30 mol %.

In one embodiment the allicin of formula (3) may be manufactured by treating a compound of formula (2), also referred to as diallyldisulphide (DADS)

(2)

with an oxidizing agent. In a useful embodiment of the method, the oxidizing agent used to oxidize compounds of formula (2) to compounds of formula (3) may be selected from the group consisting of DMDO, MCPBA, peracetic acid, potassium permanganate, magnesium oxide and Swern oxidants (e.g. oxalyl chloride, dimethyl sulfoxide (DMSO) and an organic base, such as triethylamine) DMDO is a preferred oxidant as it provides the highest yields. The oxidizing agent may be added in catalytic or stoichiometric amount relative to compound (2) but preferably in an excess amount such as 1.01-10.0 mol equivalents, preferably 1.05-5.0 mol equivalents, such as 1.07-2.0 mol equivalents, preferably 1.10 mol equivalents. The compound of formula (2) may be advantageously added to a solution of the oxidizing agent at low temperature over a period of several minutes. The concentration of oxidizing agent in the solution can be 0.001-1.0 M, preferably 0.005-0.5 M, 0.01-0.1 M, such as 0.07 M. The solution may be in a solvent capable of staying fluid at low temperatures, such as acetone, dichloromethane, chloroform, tetrachloromethane, diethylether, ethyl acetate, or tetrahydrofurane. The solution temperature while adding compound (2) may be −100° C. to 10° C., preferably −80° C. to −10° C., −60° C. to −40° C., such as −50° C. Compound (2) may be added over a period of 1-120 min, preferably 5-90 min, 7-60 min, 10-30 min, 12-20 min, such as 15 min. After addition of compound (2) to the solution, this may advantageously be allowed to warm up slowly by 10-60° C., preferably 20-40° C., such as 30° C., over a period of 10-120 min, preferably 15-90 min, 20-60 min, 25-40 min, such as 30 min. Concentration via evaporation of solvents provides the intermediate compound (3) in a crude form with a purity of at least 80 mol %, preferably at least 85 mol %, at least 90 mol %, such as at least 95 mol %.

The crude allicin (3) may be used without further purification, and still provide good yields in the following step. This could be due to the lack of acid present in the oxidation procedure, which seems to contribute to degradation of allicin during oxidation and subsequent storage. However, in a preferred embodiment allicin (3) may advantageously be purified in order to isolate a substantially allicin (3) prior to the subsequent acid treatment. This was found to provide an even cleaner reaction and higher yields in the subsequent acid treatment step to provide compounds of formula (1). The purification can be performed using any conventional purification methods, preferably silica column chromatography. Chromatography can be performed using a mobile phase eluent consisting of a mixture of diethyl ether in pentane, preferably 0.5-20 V/V % diethylelether in pentane, such as 1-10 V/V %, 2-8 V/V %, 3-7 V/V %, 4-6 V/V %, preferably 5 V/V %. Thereby a compound of formula (3) is obtained in a yield based on compound (2) of at least 80 mol %, preferably at least 85 mol %, at least 90 mol %, such as at least 95 mol %.

In a second aspect of the invention a process for making compounds of formula (4) is provided (4)

where Y is chosen from —S—, —S(O), or —S(O$_2$)—, R is chosen from allyl, phenyl, methyl, ethyl, propyl, butyl, pentyl, hexyl, benzyl, p-tolouyl, m-tolouyl, o-tolouyl, and the conformation of the internal —C=C— bond can be either E or Z or a mixture thereof. This process comprises the method as defined above to make compound of formula (1) followed by an additional reaction step involving reacting (E,Z) ajoene of formula (1) with at least one additional oxidizing reagent to provide a compound of formula (4) wherein R is allyl, and optionally reacting the compound of formula (4) with an R substituted lithiated sulphide (R-SLi) to provide compounds of formula (4) wherein R is phenyl, methyl, ethyl, propyl, butyl, pentyl, hexyl, benzyl, p-tolouyl, m-tolouyl, or o-tolouyl.

In one embodiment of the method defined above, the second oxidizing agent used to oxidize compounds of formula (1) to compounds of formula (4) may be selected from the group consisting of DMDO, MCPBA, peracetic acid, potassium permanganate, Hydrogen peroxide, Bis TMS Peroxide, or any mild peroxides. The reaction with R-substituted lithiated sulphide may be performed in tetrahydrofurane solvent at −78° C. up to 0° C. Reaction time may be 30 min to 24 hours, preferably 30 min to 2 hours.

The purification of compounds of formula (4) may be performed in a similar manner to that of compounds of formula (1) as described above.

The compounds obtained of general formula (4) can be isolated as mixtures of (E,Z)-isomers, or these isomers can be separated to provide substantially pure (E)-isomers or substantially pure (Z)-isomers. Also, the compounds of formula (4) having different oxidation states of Y, i.e. Y equal to —S—, S(O), or —S(O$_2$)— can be either separated or isolated as mixtures.

Another embodiment of the present invention is the compounds of formula (1) obtained by the methods of described above or alternatively the compounds of formula (1) obtainable by the methods of described above. As described, the above method leads to good crude purities, which leads to the use of only one chromatographic purification step, which has proved to be vital to obtain a more biologically active (E,Z)-ajoene derivative (1). Such active ajoene derivatives may be said to have a purity in the range of 95-99.5%, such as about 97-99.5%, 98-99.5%, 99-99.5% such as about 99.5%. The E:Z ratio of the (E,Z) ajoene obtained may preferably be from 20:1 to 1:10, such as from 15:1 to 1:6, 12:1 to 1:5, preferably from about 10:1 to about 1:4. Alternatively the E:Z ratio may preferably be from 1:1 to 1:10, such as from 1:2 to 1:8, 1:3 to 1:5, preferably about 1:4.

Yet a further aspect of the invention is a composition comprising a (E,Z)-ajoene having formula (1) and at least one antibiotic. The compound (i.e. (E,Z)-ajoene having an obtainable E:Z ratio including pure E or pure Z) may be obtained by the method described above, or any other methods providing a biologically active QS-inhibiting (E,Z)-ajoene product. Such compositions may be used in the formulation of medicaments and thus may be formulated as a medicament or dosage form comprising a (E,Z)-ajoene having formula (1), at least one antibiotic and pharmaceutically acceptable carriers and/or binders. The medicament may be formulated as liquid or solid dosage forms, where liquid compositions may include liquid compositions for topical administration, liquid compositions for intravenous injection, intramuscular or subcutaneous injection, or a liquid composition for inhalation as an aerosol. Solid dosage forms may include tablets, capsules, powders, including powders for inhalation. Embodiments wherein the (E,Z)-ajoene is administered in one of the above ways, while the antibiotic is administered in any other of the above ways are also inferred. For example the ajoene may be administered by inhalation, via powder or aerosol, while the antibiotic is administered intravenously.

The E:Z ratio of the (E,Z) ajoene in the composition may preferably be from 20:1 to 1:10, such as from 15:1 to 1:6, 12:1 to 1:5, preferably from about 10:1 to about 1:4. Alternatively the E:Z ratio may preferably be from 1:1 to 1:10, such as from 1:2 to 1:8, 1:3 to 1:5, preferably about 1:4.

One embodiment is thus a composition as described above comprising (E,Z)-ajoene having formula (1) and at least one antibiotic for use in the treatment of infections, preferably bacterial infections comprising biofilm forming bacteria.

An advantage of such compositions is that a synergistic effect is achieved when using a QS-inhibitor in a composition with an antibiotic, as demonstrated herein. In the context of the present invention an antibiotic is defined as any antibacterial substance where the antibacterial effect is not based on QS inhibition. Typically, the antibiotic used in combination with a QS-inhibitor can be classified as either bactericidal or bacteriostatic. Bactericidals kill bacteria directly where bacteriostatics prevent bacteria from dividing. Classes of antibiotics include aminoglycosides, ansamycins, carbacephem, carbapenems, cephalosporins, glycopeptides, macrolides, monobactams, penicillins, polypeptides, quinolones, sulfonamides, and tetracyclines. The antibiotic may be selected from any of these classes.

The antibiotic may be selected from the group consisting of Ampicillin, Bacampicillin, Carbenicillin Indanyl, Mezlocillin, Piperacillin, Ticarcillin, Amoxicillin-Clavulanic Acid, Ampicillin-Sulbactam, Benzylpenicillin, Cloxacillin, Dicloxacillin, Methicillin, Oxacillin, Penicillin G, Penicillin V, Piperacillin Tazobactam, Ticarcillin Clavulanic Acid, Nafcillin, Cefadroxil, Cefazolin, Cephalexin, Cephalothin, Cephapirin, Cephradine, Cefaclor, Cefamandol, Cefonicid, Cefotetan, Cefoxitin, Cefprozil, Ceftmetazole, Cefuroxime, Loracarbef, Cefdinir, Ceftibuten, Cefoperazone, Cefixime, Cefotaxime, Cefpodoxime proxetil, Ceftazidime, Ceftizoxime, Ceftriaxone, Cefepime, Azithromycin, Clarithromycin, Clindamycin, Dirithromycin, Erythromycin, Lincomycin, Troleandomycin, Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Perfloxacin, Imipenem-Cilastatin, Meropenem, Aztreonam, Amikacin, Gentamicin, Kanamycin, Neomycin, Netilmicin, Streptomycin, Tobramycin, Paromomycin, Teicoplanin, Vancomycin, Demeclocycline, Doxycycline, Methacycline, Minocycline, Oxytetracycline, Tetracycline, Chlortetracycline, Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Rifampin, Rifabutin, Rifampin, Rifapentine, Linezolid, Quinopristin Dalfopristin, Bacitracin, Chloramphenicol, Fosfomycin, Isoniazid, Methenamine, Metronidazol, Mupirocin, Nitrofurantoin, Nitrofurazone, Novobiocin, Polymyxin, Spectinomycin, Trimethoprim, Colistin, Cycloserine, Capreomycin, Ethionamide, Pyrazinamide, Para-aminosalicyclic acid, and Erythromycin ethylsuccinate. The antibiotic may e.g. be tobramycin.

One aspect of the present invention is (E,Z)-ajoene of formula (1) for use in treatment of bacterial infections, preferably bacterial infections comprising biofilm forming bacteria.

Another aspect of the invention is (E,Z)-ajoene of formula (1) as obtained by the herein described method for use in treatment of bacterial infections, preferably bacterial infections comprising biofilm forming bacteria.

The below described embodiments thus relates to both (E,Z)-ajoene in general, and also to (E,Z)-ajoene as provided in the herein described method and finally also to compositions comprising (E,Z)-ajoene and an antibiotic as described above.

The E:Z ratio of the (E,Z) ajoene obtained may preferably be from 20:1 to 1:10, such as from 15:1 to 1:6, 12:1 to 1:5, preferably from about 10:1 to about 1:4. Alternatively the E:Z ratio may preferably be from 1:1 to 1:10, such as from 1:2 to 1:8, 1:3 to 1:5, preferably about 1:4.

The treatment of bacterial infections, including those comprising biofilm forming bacteria, may be prophylactic. The compounds used may be in a composition with an antibiotic and/or a pharmaceutically acceptable carrier. The compounds or compositions may be administered by intravenous injections, intramuscular or subcutaneous injections, orally, topically or they may be inhaled, preferably using a suitable inhalation device. They may be inhaled as solid compositions, such as powders, or as liquid compositions in the form of aerosols.

In a one embodiment the bacterial infection treated is in a mammal with an immune deficiency. In the context of the present invention a mammal with immune deficiency is a mammal that for any reason is immuno-compromised, meaning that the performance of some or all aspects of the natural defence is lower than normal. Typically, this may be due to an immuno-compromising disease or due to therapy using immuno-suppressant medication. Such mammals are at higher risk of infections with biofilm forming bacteria such as *Pseudomonas aeruginosa* and would therefore potentially benefit from both prophylactic and acute treatment with a QS inhibitor which may be in a composition with an antibiotic. Mammals may comprise humans, pets and livestock, or mammals may be selected from the group consisting of humans, pets and livestock. Immuno-compromising diseases include diseases selected from the group consisting of cystic fibrosis, diabetes mellitus, COPD, malignant haematological disease, cancer, HIV, AIDS, chronic wounds, burn wounds. Patients may include patients with indwelling catheters, patients treated with medical equipment, implants, stents and patients in ICU's.

In a preferred embodiment of the invention the bacteria, particularly the biofilm forming bacteria causing the infections described above may be selected from the group of bacteria capable of QS controlled virulence such as gram negative bacteria, particularly the following groups of Gram negative bacteria: *Vibrio fischeri, Aeromonas hydrophila, Aeromonas salmonicida, Agrobacterium tumefaciens, Burkholderia cepacia, Chromobacterium violaceum, Enterobacter agglomerans, Erwinia carotovora, Erwinia chrysanthemi, Erwinia Stewartii, Escherichia coli, Pseudomonas aureofaciens, Pseudomonas aeruginosa, Ralstonia solanacearum, Rhizobium etli, Rhizobium leguminosarum, Rhodobacter sphaeroides, Salmonella typhimurium, Serratia liquefaciens, Sinorhizobium meliloti, Vibrio anguillarum, Vibrio harveyi, Yersinia enterocolitica, Yersinia pseudotuberculosis*, particularly *Pseudomonas aeruginosa*.

Yet an additional preferred embodiment of the present inventions is (E,Z)-ajoene of formula (1) for use in the treatment of bacterial infections where the infected area is a wound, such as a chronic wound and/or non-healing wound. In these cases the compounds may advantageously be administered topically.

Another useful embodiment is (E,Z)-ajoene of formula (1) for use in the treatment of bacterial infections where the infected area is the lungs. This treatment is especially relevant for cystic fibrosis patients who, due to their reduced immune response, often suffer from persistent lung infections comprising biofilm forming bacteria, such as *Pseudomonas aeruginosa*. Therefore, a preferred embodiment is (E,Z)-ajoene of formula (1) for use in the treatment of bacterial infections where the infected area is the lungs of a cystic fibrosis patient. In these cases the compounds may advantageously be administered via inhalation or by intravenous injections.

In another preferred embodiment the infected area is an implant or the area around an implant. As defined herein an implant is a medical device made to replace or act as a missing biological structure in a mammal. Such implants may include implants containing electronics such as artificial pacemakers and cochlear implants, subcutaneous drug delivery devices in the form of implantable pills or drug-eluting stents, a prosthetic device such as bone-replacement and support devices or dental implants.

In yet another embodiment the infected area may be the part of the digestive system, such as the stomach and/or intestines. Such infections may include food poisoning or infections arising from pancreatic or biliary stents.

It should be noted that embodiments and features described in the context of one of the aspects of the present invention also apply to the other aspects of the invention. Also, all of the above embodiments above describing compounds and compositions for use in the treatment of various indications, may all equally be described as methods of treating said indication by administration of the said compounds or compositions.

All patent and non-patent references cited in the present application, are hereby incorporated by reference in their entirety.

The invention will now be described in further details in the following non-limiting examples.

EXAMPLES

Example 1: Synthesis of Compound (3), Allicin

An acetone solution of DMDO (31 mL, 0.07M, 2.2 mmol) was added dropwise over 15 min to compound (2), diallyldisulphide (0.29 g, 2.0 mmol) in acetone (1 mL) at −50° C. under argon. The resulting light yellow reaction mixture was allowed to stir for 30 min while slowly warming to −20° C. The resulting clear reaction mixture was concentrated in vacuo. The crude residue (0.31 g, 98%) was further purified by column chromatography (eluting with 5% $Et_2O$ in pentane) to yield compound (3), allicin (0.31 g, 1.9 mmol, 96% yield, purity >95% and up to 99.9%) as a light yellow liquid.

The above reaction was repeated under varying condition with respect to solvent and temperature. Remaining parameters were kept the same. As seen in table 1 below the reaction is effective under a number of conditions.

TABLE 1

Conversion of diallyldisulphide to allicin (3)

| Entry | Solvent | Temp | 2/Yield |
|---|---|---|---|
| 1 | Acetone | −100° C., 78° C., −50--20° C. | 96% |
| 2 | $CH_2Cl_2$ | −100° C., 78° C., −50--20° C. | 90% |
| 3 | $CHCl_3$ | −78--60° C. | 92% |
| 4 | $CCl_4$ | −78--60° C. | 96% |
| 5 | $Et_2O$ | −50--20° C. | 86% |
| 6 | EtOAc | −50--20° C. | 80% |
| 7 | THF | −50--20° C. | 85% |

Example 2: Synthesis of Compound (1), (E,Z)-Ajoene Using Acetone Solvent

A solution of compound (3), allicin (0.162 g, 1.0 mmol) in a 40% aqueous acetone solution (1.6 mL) was treated with AcOH (0.011 mL, 0.2 mmol). The resulting mixture was heated to 64° C. for 4 h. The cooled reaction mixture was diluted with 50% aqueous methanol (6 mL) and extracted with pentane (5×10 mL). The aqueous fraction was saturated with solid NH4SO4 and the mixture was extracted with $CH_2Cl_2$ (5×10 mL). The combined organic extracts were dried ($Na_2SO_4$) and concentrated in vacuo. The crude residue (0.16 g) was further purified by column chromatography (eluting with 60-80% EtOAc in pentane) to yield compound (1), (E,Z)-ajoene (E:Z ratio=1:4, 0.025 g, 0.1 mmol, 32% yield) as a light yellow liquid.

The above reaction was repeated using a variety of acids. Remaining parameters were kept the same as above. Exchange of acid had impact on both yields and E:Z ratios of ajoene as seen in table 2 below:

TABLE 2 conversion of allicin (3) to (E, Z) ajoene (1) using different acids.

| Entry | Acid | Conditions | Yield (E:Z) |
|---|---|---|---|
| 1 | TsOH | 40% aq. acetone, 64° C., 4 h | 24 (1:4) |
| 2 | CSA | 40% aq. acetone, 64° C., 4 h | 20 (1:5) |
| 3 | MsOH | 40% aq. acetone, 64° C., 4 h | 22 (1:4) |
| 4 | TFA | 40% aq. acetone, 64° C., 4 h | 12 (1:1) |

Importantly, it was found that when using less than highly pure allicin (3) the yields in the above reactions were drastically reduced, if not zero. It was also found that when using the methods of the prior art to obtain allicin (3), some impurities stemming from either garlic extract or the reactants or the products used in the block synthesis of allicin resulted in yields of ajoene no higher than 6-12%. This applied regardless of which solvent and acid was used for the ajoene synthesis.

Example 3: Synthesis of Compound (1), (E,Z)-Ajoene [E:Z=10:1]

A solution of compound (3), allicin (0.162 g, 1.0 mmol) in a 10% aqueous benzene solution (1.6 mL) was treated with AcOH (0.011 mL, 0.2 mmol). The resulting mixture was heated to 37° C. for 48 h. The cooled reaction mixture was diluted with 50% aqueous methanol (6 mL) and extracted with pentane (5×10 mL). The aqueous fraction was saturated with solid $NH_4SO_4$ and the mixture was extracted with $CH_2Cl_2$ (5×10 mL). The combined organic extracts were dried ($Na_2SO_4$) and concentrated in vacuo. The crude residue (0.15 g) was further purified by column chromatography (eluting with 60-80% EtOAc in pentane) to yield compound (1) (E,Z)-ajoene (E:Z ratio 10:1, 0.023 g, 0.1 mmol, 30% yield) as a light yellow liquid.

Example 4: Synthesis of a Compounds of Formula (4)

Figure 1:
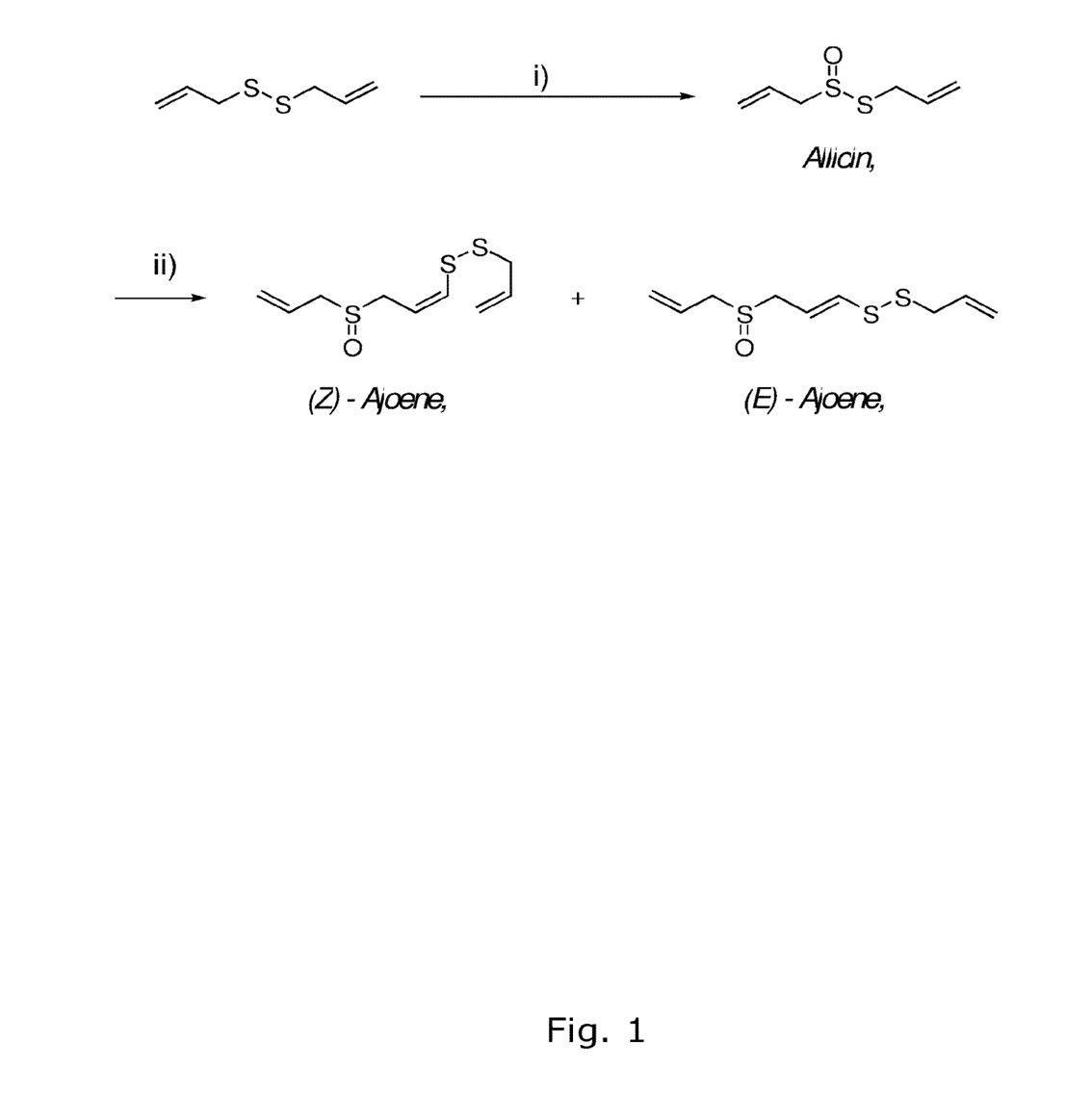
FIG. 1 shows an exemplary scheme depicting the synthetic route towards (E,Z)-ajoene derivatives, including control of E:Z ratio of isomers. The reaction conditions conditions were i) Dimethyldioxirane (DMDO), acetone, −50° C. to −20° C., 30 min, 96% yield; ii) either A) 20% AcOH, 40% aqueous acetone, 64° C., 4 h, 36% yield, (Z:E–4:1) or B) 20% AcOH, 40% toluene, 40° C., 48 h, 32% yield, (Z:E– 1:10).
Figure 2:
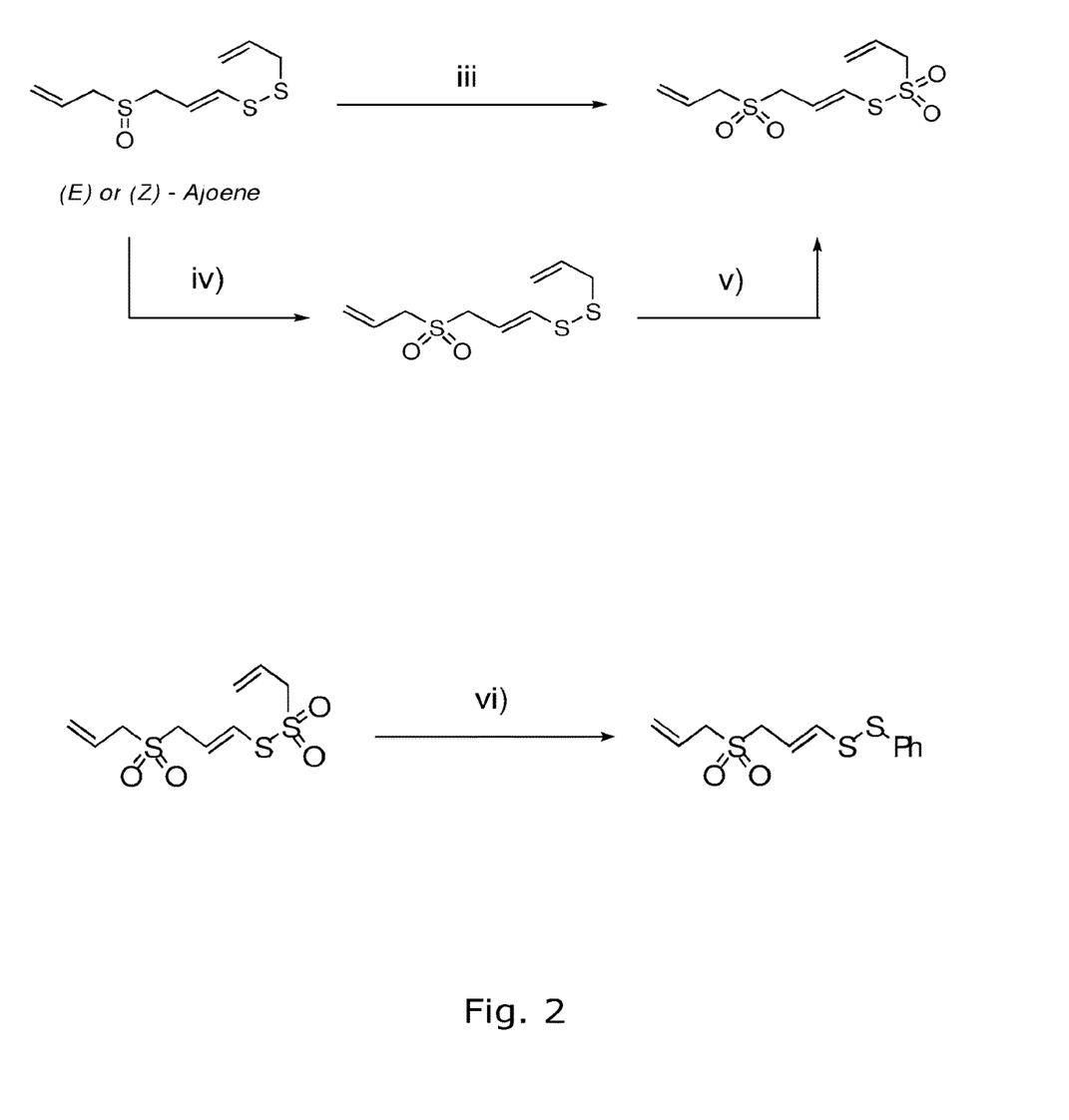

Oxidized sulphone derivatives of (E,Z) ajoene has been shown to have QS inhibitory effects. Therefore such derivatives, i.e. compounds of formula (4) were synthesized using various routes as described below (see also FIG. 2):

Y=S, R=allyl

The compound of formula (1) ((E,Z) Ajoene) was treated with potassium permanganate ($KMnO_4$) in acetone at −20° C. for 2 hours to obtain a compound of formular (4) with Y=S and R=allyl in 96% yield. Workup and purification was analogous to that used for (E,Z) ajoene.

Y=S(O)$_2$, R=allyl

The compound of formula (1) ((E,Z) Ajoene) was treated with peracetic acid in dichloromethane at 0° C. for 12 hours to obtain a compound of formular (4) with S(O)$_2$, R=allyl in 38% yield. Workup and purification was analogous to that used for (E,Z) ajoene.

Alternatively, the compound of formula (1) ((E,Z) Ajoene) was treated with 4 equivalents of DMDO in acetone at −10° C. for 6 hours to obtain a compound of formular (4) with S(O)$_2$, R=allyl in 82% yield. Workup and purification was analogous to that used for (E,Z) ajoene.

In yet another alternative route the compound of formula (4) with Y=S and R=allyl as described above was treated with 2 equivalents of DMDO in acetone at −10° C. for 6 hours to obtain a compound of formular (4) with S(O)$_2$, R=allyl in 78% yield.

Y=S, R=phenyl

The compound of formula (4) where Y=S(O)$_2$, R=allyl was treated with lithiated sulphide (PhSLi) in tetrahydrofurane at a temperature of −78° C. which was allowed to rise to 0° C. over 1 hour to obtain the compound of formula (4) having Y=S, R=phenyl in 86% molar yield.

Y=S, R=methyl, ethyl, benzyl

In analogy to the method above where Y=S, R=phenyl, the corresponding compounds of formula (4) with R=methyl, ethyl, benzyl was produced in similar yields using the corresponding lithiated sulphides (i.e. MeSLi, EtSLi and allylSLi). Remaining parameters were kept the same.

Example 5: P. aeruginosa Genes Regulated by Ajoene Treatment

DNA microarray analysis was used to identify genes regulated by ajoene treatment. As a reference we have used the QS regulon previously identified by Hentzer et al., [M. Hentzer et al., EMBO J., 2003, 22, p. 3803-3815] and these data has been used to validate target specificity of putative quorum sensing inhibiting (QSI) compounds. Exponential growing P. aeruginosa cultures were treated with the following four concentrations of ajoene; 10 μg/ml (42.7 μM), 20 μg/ml (85.4 μM), 40 μg/ml (170.8 μM) and 80 μg/ml (341.6 μM). (E,Z) ajoene having an E:Z ratio of 1:4 was used. These concentrations do not exert any growth inhibitory effects. The samples were retrieved at an OD600 nm of 2.0 (optical density) because previous investigations have shown the highest activity among the QS genes at that cell density. Gene expression of the treated cultures was compared to an untreated control.

In general, there was only a small number of genes that were down regulated more than 5 fold by the four different concentrations of ajoene; 0 genes at 10 μg/ml ajoene, 0 genes at 20 μg/ml ajoene, 2 genes at 40 μg/ml ajoene and 11 genes at 80 μg/ml ajoene. The amount of genes up regulated more than 5 fold did not vary noticeably between the treated cultures. According to our experimental settings, expression of 10 out of the total number of 163 QS controlled P. aeruginosa genes (according to Hentzer et al., [M. Hentzer et al., EMBO J., 2003, 22, p. 3803-3815]) was down regulated by the ajoene treatments. A concentration of 80 μg/ml ajoene affects expression of 11 out of a total of 5570 P. aeruginosa genes. Ajoene is therefore highly specific for a subclass of QS controlled genes (Table 3).

TABLE 3

Alterations in gene expression by ajoene. Genes included are >5 times down regulated by 80 μg/ml ajoene treatment. The numbers are fold change in gene expression compared to an untreated control. Data represent the average of tree individual experiments.

| Gene No | Gene | [Ajoene] μg/ml | | | | Description |
|---|---|---|---|---|---|---|
| | | 10 | 20 | 40 | 80 | |
| PA0852 | cbpD | −2.8 | −2.5 | −3.9 | −6.9 | Chitin-binding protein |
| PA1871 | lasA | −2.6 | −2.2 | −3.0 | −8.7 | LasA protease precursor |
| PA2069 | — | −2.3 | −2.4 | −4.0 | −5.3 | Probable carbamoyl transferase |
| PA2146 | — | −1.3 | −1.8 | −2.6 | −7.3 | Conserved hypothetical protein |
| PA2300 | chic | −2.5 | −2.1 | −5.1 | −24.6 | Chitinase |
| PA2570 | pa1L | −1.8 | −2.0 | −3.3 | −6.3 | LecA |
| PA3478 | rhlB | −2.6 | −2.0 | −3.3 | −8.7 | Rhamnosyltransferase chain B |
| PA3479 | rhlA | −2.2 | −1.5 | −2.6 | −8.8 | Rhamnosyltransferase chain A |
| PA4141 | — | −1.0 | −1.1 | −1.3 | −5.4 | Hypothetical protein |
| PA4142 | — | −2.0 | −2.2 | −2.7 | −5.1 | Probable secretion protein |
| PA4175 | prpL | −3.7 | −3.3 | −5.3 | −6.8 | Pvds-regulated endoprotease |

\* Indicates P < 0.05,
\*\* indicates P < 0.01,
Student's t-test.

Among the genes significantly down-regulated by ajoene were the following QS regulated important virulence factors, LasA protease (lasA, PA1871), chitinase (chiC, PA2300), the cytotoxic galactophilic lectin (lecA, PA2570), the rhamnosyl transferase AB operon (rhlA, PA3478 and rhlB, PA3479), the PvdS-regulated endoprotease (prpL, PA4175) that degrades casein, elastin, lactoferrin, transferrin, and decorin, and the associated chitin-binding protein cbpD (PA0852) which mediates attachment to chitin-containing substrates and presumably assist in biofilm formation. lasB was not more than 5-fold down regulated.

Example 6: Verification of the Microarray Data

Figure 3:
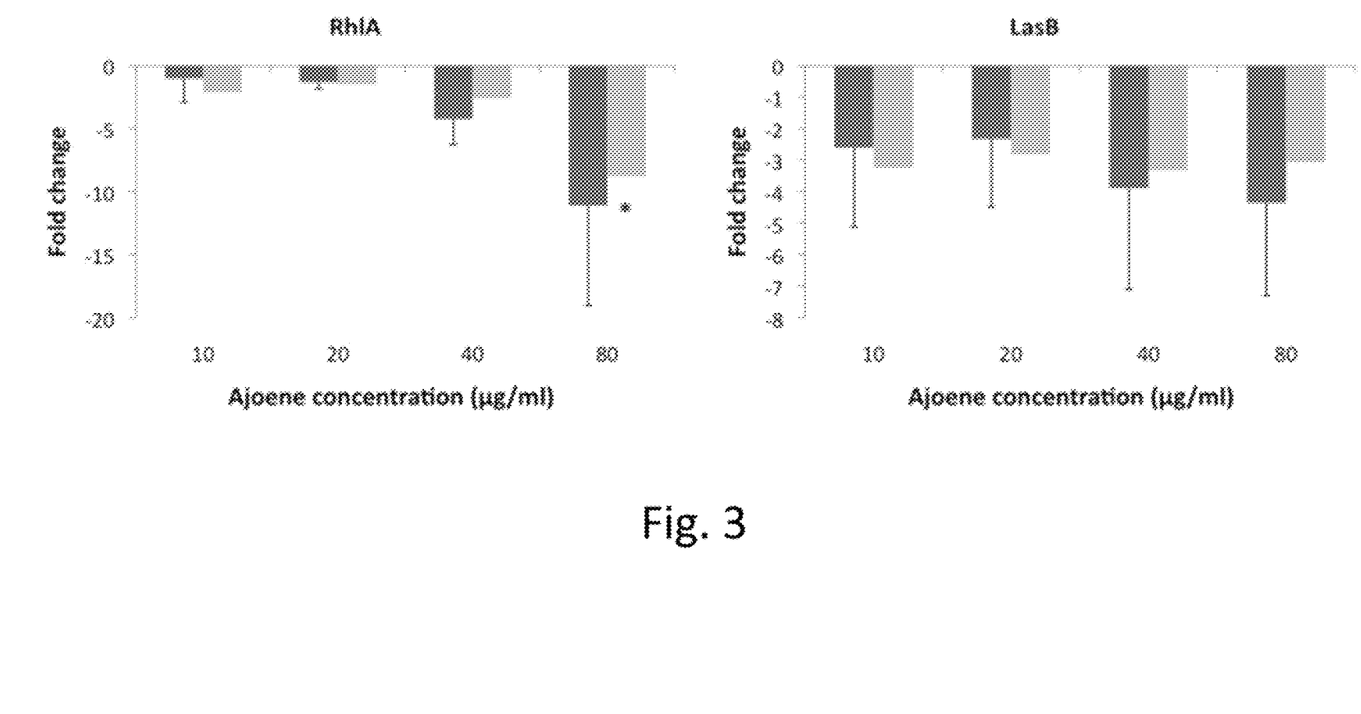
FIG. 3 shows a comparison of fold change (– indicates down regulation) in gene expression of rhlA and lasB as measured by RT-PCR (dark grey bars) and DNA microarray (light grey bars). Data represent the average of tree individual experiments. A star (*) indicates P<0.05, Student's t-test. Error bars are mean±SD.
Figure 4:
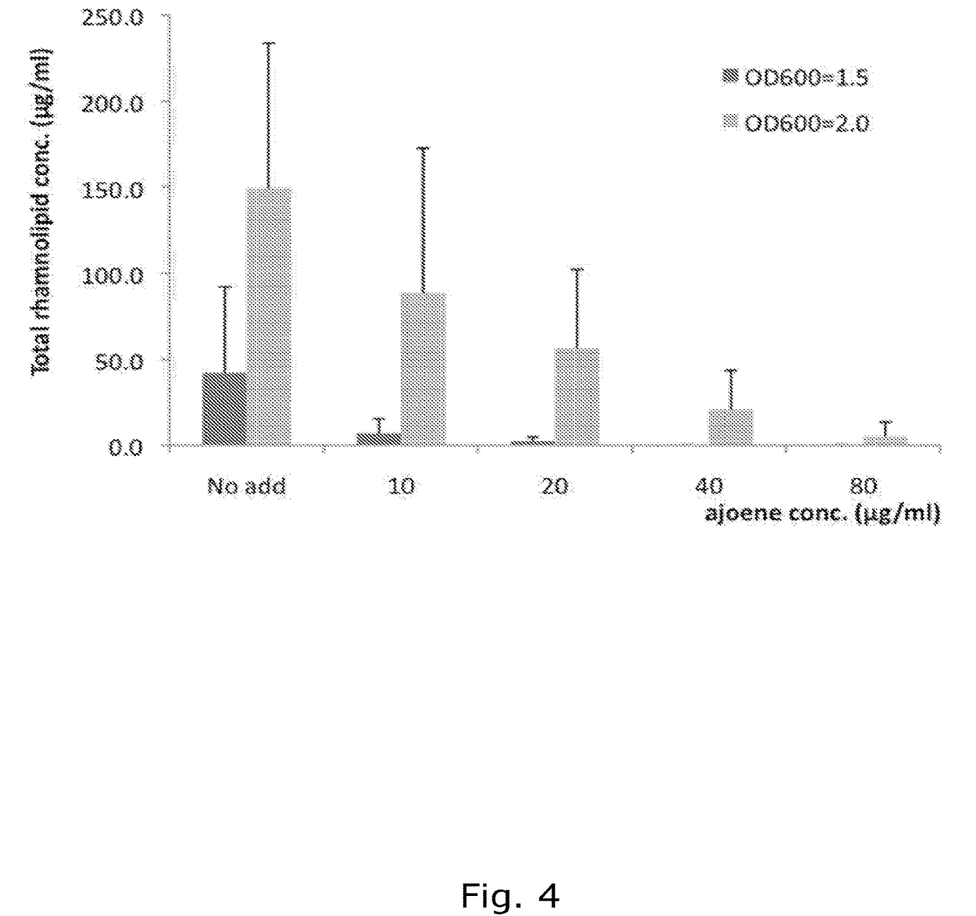
FIG. 4 shows total rhamnolipid concentration in untreated ("no add") and ajoene treated planktonic grown *P. aeruginosa*. The cultures were grown in medium supplemented with 10 μg/ml, 20 μg/ml, 40 μg/ml and 80 μg/ml of ajoene (at 40 μg/ml and at 80 μg/ml the rhamnolipid content is below the detection level at OD=1.5). Samples retrieved at OD600=1.5 (dark grey bars), and at OD600=2.0 (light grey bars). Data represent the average of tree individual experiments. Error bars are mean±SD.

To verify the microarray data, RT-PCR was performed with two of the key QS genes; lasB and rhlA (see FIG. 3). When comparing the two methods the repression of both the lasB and rhlA gene expression follow the same trend, with a general slightly increase in fold reduction observed with the RT-PCR based method. The RT-PCR data shows that a concentration of 80 μg/ml ajoene lowers the expression of rhlA almost 12 fold and lasB almost 5 fold. The expression of rhlA is primarily controlled by the Rhl QS system and the signal molecule BHL whereas the expression of lasB is affected by both the Las and the Rhl QS systems and the concentration of the signal molecules OdDHL and BHL. According to Rasmussen et al., [Rasmussen et al., Microbiology, 2005, 151, p. 1325-1340], the genes listed in table 3 are (except prpL which regulation is entirely governed by the Las QS system) subject to regulation by both the Las and Rhl QS systems. This suggests that ajoene primarily targets the Rhl QS. (E,Z) ajoene having an E:Z ratio of 1:4 was used in these experiments.

Example 7: Attenuation of Rhamnolipid Production by Ajoene

To exemplify the actual efficacy of ajoene in inhibiting synthesis of one of the major virulence factors, the concentration of rhamnolipid present in the cultures grown for DNA array and RT-PCR where directly quantified by LC-MS. The production of rhamnolipids is initiated early in stationary phase co-ordinately regulated by the Rhl QS system encoded by the rhlA, rhlB and rhlC genes (PA3479, PA3478 and PA1131) [V. E. Wagner et al., J Bacteriol., 2003, 185, p. 2080-2095 and R. Rahim et al., Mol Microbiol., 2001, 40, p. 708-718]. Samples where therefore retrieved at an OD600 nm of 1.5 and 2.0 to monitor rhamnolipid production before and after the synthesis was fully initiated. The concentration of rhamnolipid in the samples was found to be gradually decreased with increasing concentration of ajoene. When treated with 20 μg/ml ajoene at an OD600 nm of 2.0, the rhamnolipid content were reduced to approximately ⅓ compared to the untreated culture and there was almost no detectable rhamnolipid present in the sample when the cells were treated with 80 μg/ml ajoene. This concentration therefore almost completely blocks rhamnolipid synthesis. (E,Z) ajoene having an E:Z ratio of 1:4 was used.

Figure 5:
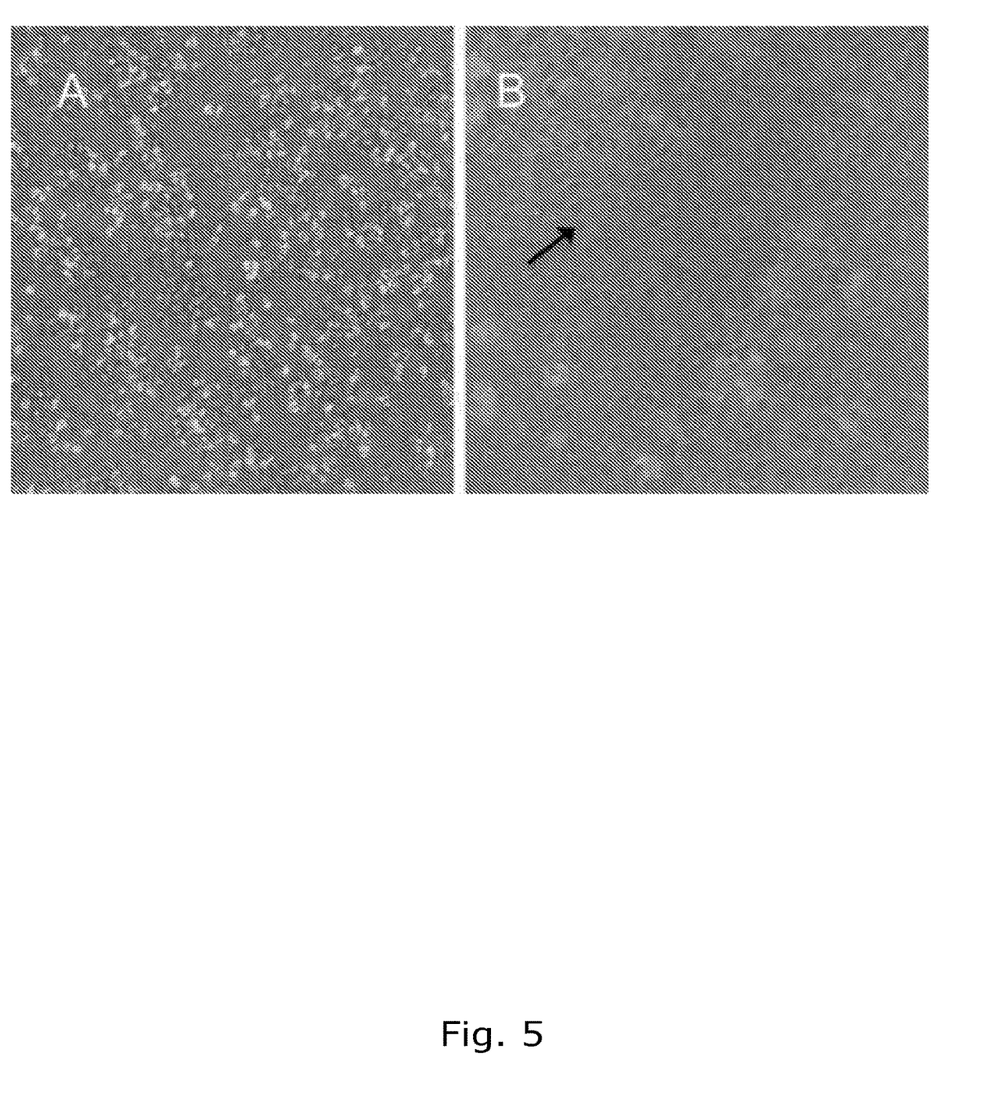
FIG. 5 Shows combined fluorescence and light microscopic investigations of biofilms of *P. aeruginosa* exposed to PMNs (a single PMN pointed out by the arrow) at day four for 180 min at 37° C. and then subsequently stained with the DNA stain propidium iodide (PI). A) The biofilm has grown without ajoene in the medium. B) The biofilm has grown in the presence of 100 μg/mL ajoene in the medium. Red fluorescence indicates necrotic PMN's leaking out their content of DNA (as stained by PI). Green fluorescence indicates top areas of the *P. aeruginosa* biofilm.

Example 8: Ajoene Treatment Renders In Vitro Biofilms Rhamnolipid Deficient and Prevents the Killing of PMNs Biofilms exposed to PMN leukocytes produce rhamnolipids that function as a shield and protects the biofilm bacteria from phagocytosis. The influence of ajoene on the lysis of PMNs was demonstrated by using an in vitro continuous-culture once through flow chamber biofilm system [B. B. Christensen et al., Methods Enzymol., 1999, 310, p. 20-42]. The *P. aeruginosa* biofilms were grown for four days either in the presence or absence of 100 μg/ml ajoene. When PMNs subsequently were introduced in the flow chambers on top of the biofilms grown in the absence of ajoene, propidium iodide (PI) staining indicated necrosis of the PMNs (FIG. 5A). In contrast, when the biofilm was grown in the presence of ajoene no necrosis of the PMNs was observed (FIG. 5B). Ajoene treatment therefore rescues the PMN leukocytes by blocking biofilm synthesis of ajoene. It has previously been shown that rescued PMN's can phagocytose biofilm bacteria [T. Bjarnsholt et al., Microbiology, 2005, 151, p. 3873-3880]. (E,Z) ajoene having an E:Z ratio of 1:4 was used.

Example 9: In Vitro and In Vivo Conformation of Synergistic Effect of Treatment with Ajoene and Antibiotics One important issue in the treatment of bacterial biofilm infections is the lowered effectiveness of administered antibiotics. An infection in the airways of CF patients will result in high concentrations of anionic polyelectrolytes like DNA [T. Brandt et al., Thorax, 1995, 50, p. 880-882] released from lysed inflammatory cells such as PMN's and bacteria. It has been showed that anionic polyelectrolytes and in particularly DNA binds to and reduce the activity of cationic antibiotics like tobramycin which can lead to a decrease in the biological available tobramycin to as low as 5% of the existing quantity [P. M. Mendelman, 1985, Am Rev Respir Dis., 132, p. 761-765]. This suggests that by blocking the production and release of rhamnolipids and eDNA, it is possible to reduce the following inactivation of tobramycin.

Figure 6:
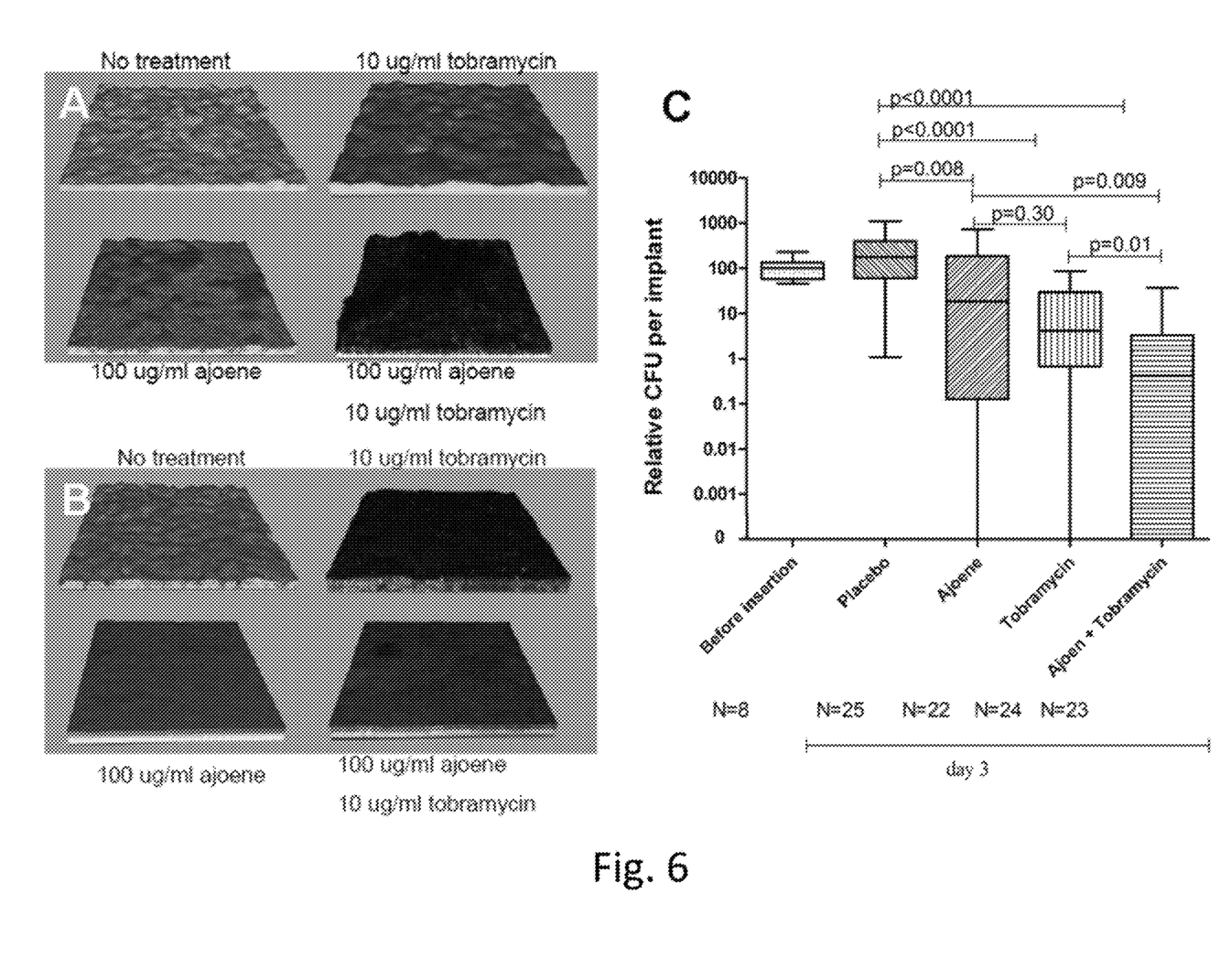
FIG. 6 shows biofilms of *P. aeruginosa* PAO1 (light grey) (A) and a clinical *P. aeruginosa* isolate CF438 (light grey, stained with syto9) (B) at day four after 24 hours with 10 μg/ml tobramycin treatment. Dead cells are stained with the DNA stain PI (Dark grey/black). The biofilm were visualized with CSLM. C) Implant model treated with ajoene and tobramycin.

In concordance with that, we have previously published that combination treatment with garlic extract and the antibiotic tobramycin of a three day old biofilm (grown in vitro in the continuous-culture, once-through flow cells) showed a synergistic killing effect [T. Bjarnsholt et al., Microbiology, 2005, 151, p. 3873-3880]. It was however unknown what was the active ingredient in the garlic extract. Thus. biofilms of *P. aeruginosa* strain were either grown in the presence or absence of 100 μg/ml ajoene. At day three the biofilms were treated with 10 μg/ml tobramycin for 24 hours. A prior treatment study indicated that treatment with 10 μg/ml, 100 μg/ml or 340 μg/ml would show no difference in the extent of killing. 10 μg/ml tobramycin was therefore chosen for the present study. The killing efficacy was evaluated using live dead stains and confocal scanning laser microscopy (CSLM) and showed almost 100% killing of the biofilm grown in the presence of ajoene [ajoene had not been subject to e.g. HPLC purification] and subsequently treated with tobramycin (FIG. 6A). This synergistic effect was also evaluated using the clinical CF isolate CF438 (a first isolate from a diagnosed CF child) which possesses functional QS systems and again almost 100% killing of the biofilm were detected (FIG. 6B).

To examine the effect of a combination treatment with ajoene and tobramycin in vivo we used an foreign-body infection model [L. D. Christensen et al., Microbiology, 2007, 153, p. 2312-2320]. Silicone tube implants with a size of 4 mm (inner diameter 4 mm/outer diameter 6 mm) pre-colonized with wild-type *P. aeruginosa*, were inserted into the peritoneal cavity of mice. Treatments were injected subcutaneously every 24 hours, where ajoene and tobramycin treatment were initiated two days pre-insertion and 24 hours post-insertion, respectively. 72 hours after insertion the implants were removed from the mice and the number of colony-forming units per implant was determined. We found that treatment of wild-type *P. aeruginosa* with a combination of ajoene and tobramycin resulted in a significant faster clearing of the implants as compared to both the placebo group and the single treatments with ajoene or tobramycin ($p<0.0001$, $p=0.009$ and $p=0.01$, respectively). A significant difference in clearing was also observed between the placebo group and the single treatment groups ($p=0.008$ and $p<0.0001$). We found no significant difference in clearing between the two single treatment groups (p=30) (FIG. 6C). (E,Z) ajoene having an E:Z ratio of 1:4 was used.

We have shown in vitro that addition of 100 µg/ml ajoene to a biofilm followed by addition of 10 µg/ml tobramycin kills almost 100% of the biofilm whereas the presence of tobramycin or ajoene only results in no or only minor killing of the biofilm bacteria. It is documented that the release of eDNA is controlled by QS which taking into consideration and combined with our results points to a possible attenuation of the release of eDNA by ajoene.

Example 10: Ajoene Treatment of a Pulmonary *P. aeruginosa* Infection

Figure 7:
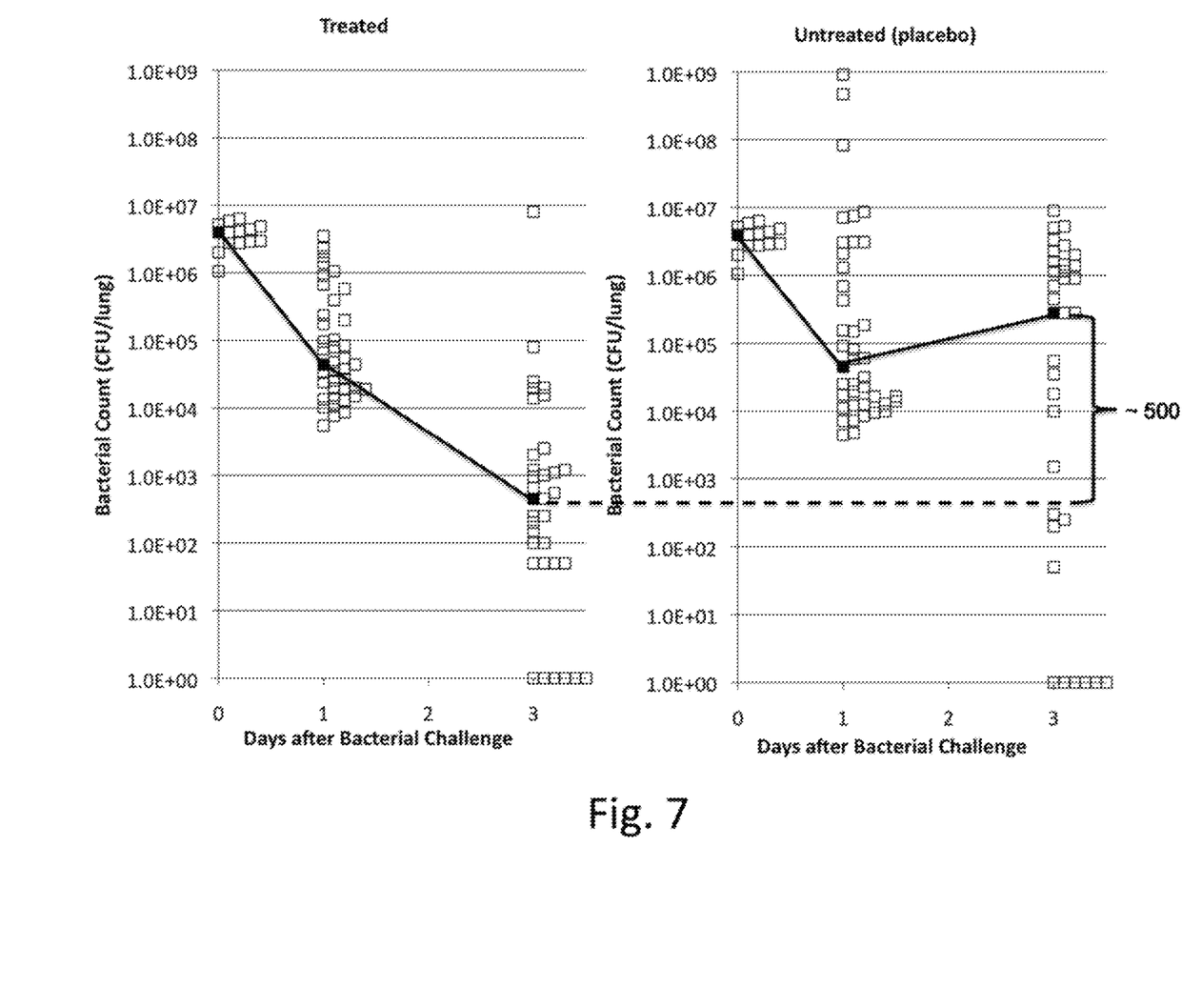
FIG. 7 shows combined results of three separate experiments of ajoene treatment versus no treatment (placebo) using the pulmonary infectious mouse model. Mice were sacrificed on day one or day three post-infection and the contents of bacteria in the lungs were determined. Open squares indicate bacterial lung content per lung for each individual mouse. The median values are indicated with a filled black square. The statistic significance of difference in clearance was tested by a Mann-Whitney U test (analysis of nonparametric data) and p-values for the difference at day one and day three were 0.9 and 0.002 respectively.

In this study ajoene was administered prophylactic and subsequently continued after infection. Injections were given subcutaneous in the peritoneum. We performed three individual in vivo treatment experiments with ajoene in the mouse model of pulmonary infection using the *P. aeruginosa* PAO1. BALB/c mice were intracheally challenged (at day 0) with alginate beads containing $1.5 \times 10^8$ CFU/ml *P. aeruginosa*. The two groups of mice were either untreated (placebo) or treated with ajoene 25 µg/g mouse once a day. The mice were given two days of prophylactic treatment or placebo prior to bacterial challenge. Treatment was continued for three days. Enumeration by plate counts showed a significant difference between the treated group and the control group on day three. When combining the experiments a significant difference on day three was seen (p<0.002) with a 500 fold difference in clearance between the groups (FIG. 7). This is concordant with the results obtained by Bjarnsholt et al (2005) in a similar lung infection model in with raw garlic extract was used as treatment [T. Bjarnsholt et al., Microbiology, 2005, 151, p. 3873-3880]. The mice tolerated well the administered dosage of 25 µg/g body weight.

Figure 8:
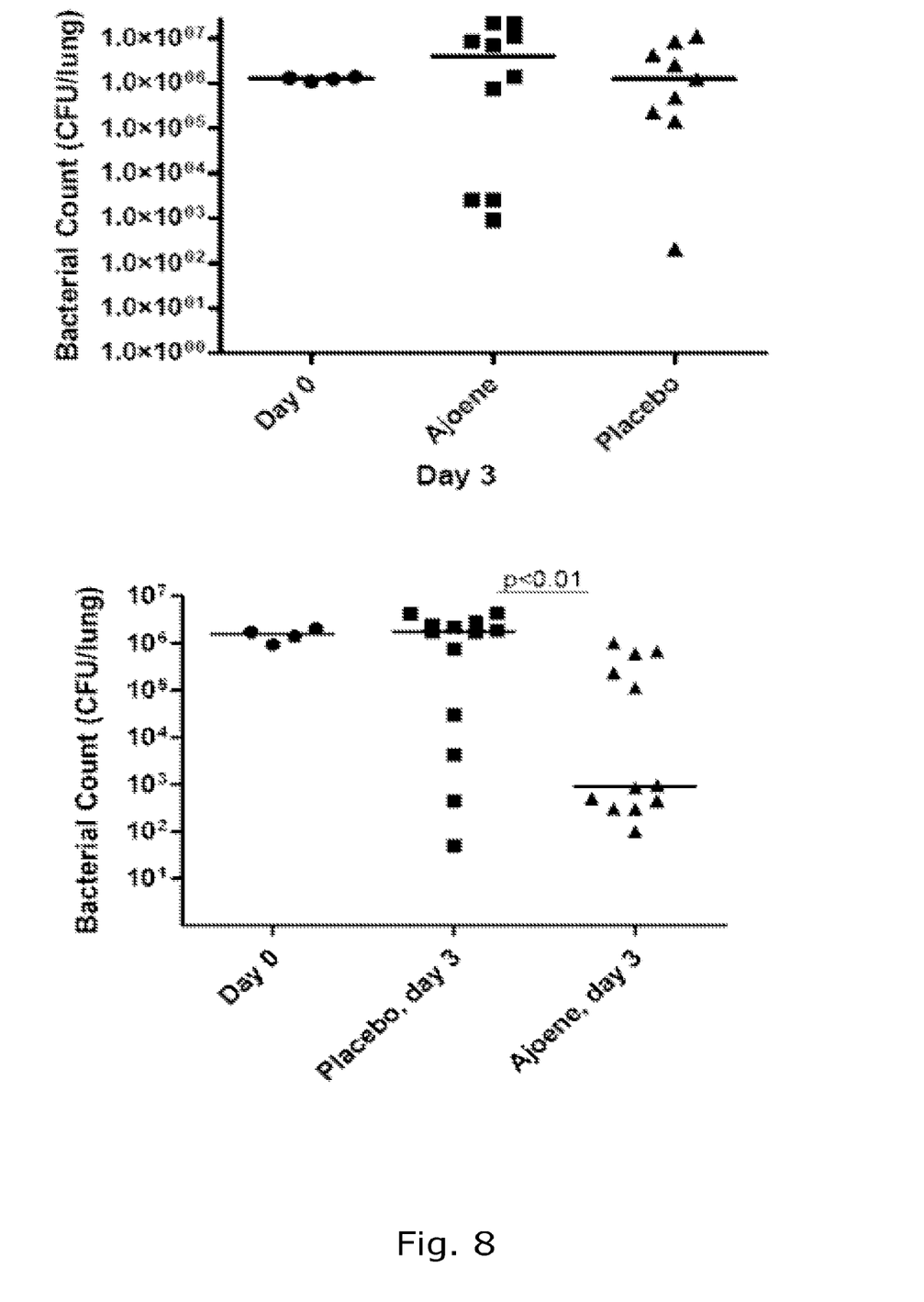
FIG. 8 shows results of experiments of treatment with HPLC purified ajoene (top graph, ajoene purity >99.5%) and ajoene which have not been HPLC purified (bottom graph, purity 95-99.5%) versus no treatment (placebo) using the pulmonary infectious mouse model. Mice were sacrificed on day three post-infection and the contents of bacteria in the lungs were determined.

Similar experiments comparing the ability of ajoene to induce clearance of *P. aeruginosa* infections as described above, when used at very high purity (>99.5%, HPLC purified) or at purities from 95% to 99.5%, (i.e. crude ajoene or ajoene subject to a single column chromatography step) demonstrated that very high purity ajoene was not effective at clearing the pulmonary infection while 95-99.5% purity ajoene was (FIG. 8, top and bottom graph respectively). This highlights that a synthesis providing a sufficiently pure "crude" ajoene product is essential in order to avoid the use of HPLC purification, as this step has a detrimental effect on biological activity. Hence, the present process providing ajoene in a purity above 95% and below 99.5% after workup and optionally column chromatography has a surprising advantage over the prior art. (E,Z) ajoene having an E:Z ratio of 1:4 was used.

When comparing the present studies with ajoene to earlier studies with garlic extracts, the present study offers a convincing indication of ajoene and close derivatives being the major active components in garlic able to reduce a *P. aeruginosa* infection.

Conclusion

In conclusion we have demonstrated the use of ajoene to attenuate virulence of *P. aeruginosa* in vivo by inhibiting transcription of a handful of important QS controlled virulence genes in *P. aeruginosa*. From our transcriptome analysis we have suggested a possible target of ajoene being the Rhl QS system. It is worth to acknowledge that QS inhibition does not remove the *P. aeruginosa* capability of forming a biofilm. However, all available data indicate that a QS deficient biofilm however is more fragile compared to the QS proficient biofilm. Since for example the matrix component DNA is missing (matrix production is Rhl QS controlled) the biofilm is sensitive to sheer forces and can slough off dependent on the hydrodynamic forces. In addition, since rhamnolipid is not formed, the biofilm becomes sensitive to the action of PMNs (because the PMNs are not killed when they get in contact with the biofilm). We have previously shown that in vitro biofilms of QS deficient bacteria can be phagocytosed by freshly isolated PMNs in contrast to QS proficient biofilms. Central for biofilm tolerance to PMNs is that rhamnolipid production forms a protective shield against the incoming PMNs and we have several data supporting that this is also the case. Using QS inhibitors should therefore greatly enhance the antimicrobial properties of the PMNs and allow them to efficiently eradicate biofilm forming bacteria. Furthermore, rhamnolipid lyses the PMNs that subsequently spill out their content of DNA, hydrolytic enzymes and oxygen radicals. This creates an "evil circle" particularly with respect to tissue damage, increasing inflammation and induction of mutations in *P. aeruginosa* of which appearance of the mucoid phenotype significantly contributes to exacerbations.

The decrease in infection in the mouse experiments, the removal of in vitro biofilm in a combinatorial experiment with tobramycin suggests the potentials of using ajoene as a future antimicrobial drug for treatment of chronic *P. aeruginosa* infections.

REFERENCES

W. C. Fuqua et al., J. Bacteriol., 1994, 176, p 269-275
T. Bjarnsholt et al., Microbiology, 2005, 151, p. 3873-3880
R. Naganawa et al., Applied and Environmental Microbiology, 62, 1996, p. 4238-4242
EP 185324
Block et al., J. Am. Chem. Soc., 1986, 108, p. 7045-7055
U.S. Pat. No. 4,665,088
WO 2010/100486
M. Hentzer et al., EMBO 3., 2003, 22, p. 3803-3815
Rasmussen et al., Microbiology, 2005, 151, p. 1325-1340
[V. E. Wagner et al., J Bacteriol., 2003, 185, p. 2080-2095
R. Rahim et al., Mol Microbiol., 2001, 40, p. 708-718]
B. B. Christensen et al., Methods Enzymol., 1999, 310, p. 20-42
T. Brandt et al., Thorax, 1995, 50, p. 880-882
P. M. Mendelman, 1985, Am Rev Respir Dis., 132, p. 761-765
L. D. Christensen et al., Microbiology, 2007, 153, p. 2312-2320

The invention claimed is:

1. A method for inhibiting virulence of a bacteria in a mammal in need thereof, comprising:
   a) selecting a mammal having an infection caused by a biofilm forming bacteria, wherein the bacteria is *Pseudomonas aeruginosa*; and
   b) administering to the selected mammal a therapeutically effective amount of ajoene formula (I):

(1)

2. The method of claim 1, wherein the bacterial infection is a pulmonary infection.

3. The method of claim 1, wherein the bacterial infection is present in a chronic wound of the selected mammal.

4. The method of claim 1, wherein the ajoene has a concentration of around 10 to 80 ug/ml.

5. The method of claim 1, wherein the dose of ajoene administered to the selected mammal is 25 ug/g body weight.

6. The method of claim 1, wherein the ajoene is a mixture of an E-isomer and a Z-isomer.

7. The method of claim 6, wherein ratio of the E- and Z-isomers in the mixture is 20:1 to 1:10.

8. The method of claim 1, wherein the selected mammal has an immune deficiency and the selected mammal is a human, pet or livestock.

9. The method according to claim 8, wherein the immune deficiency is an immuno-compromising disease or the selected mammal is taking an immuno-suppressant medication.

10. The method of claim 1, wherein the selected mammal is a cystic fibrosis patient.

11. The method of claim 1, further comprising providing at least one antibiotic selected from the group consisting of aminoglycosides, ansamycins, carbacephem, carbapenems, cephalosporins, glycopeptides, macrolides, monobactams, penicillins, polypeptides, quinolones, sulfonamides, and tetracyclines.

12. The method according to claim 11, wherein the antibiotic is an aminoglycoside.

13. The method according to claim 12, wherein the antibiotic is selected from the group consisting of Ampicillin, Bacampicillin, Carbenicillin Indanyl, Mezlocillin, Piperacillin, Ticarcillin, Amoxicillin-Clavulanic Acid, Ampicillin-Sulbactam, Benzylpenicillin, Cloxacillin, Dicloxacillin, Methicillin, Oxacillin, Penicillin G, Penicillin V, Piperacillin Tazobactam, Ticarcillin Clavulanic Acid, Nafcillin, Cefadroxil, Cefazolin, Cephalexin, Cephalothin, Cephapirin, Cephradine, Cefaclor, Cefamandol, Cefonicid, Cefotetan, Cefoxitin, Cefprozil, Ceftmetazole, Cefuroxime, Loracarbef, Cefdinir, Ceftibuten, Cefoperazone, Cefixime, Cefotaxime, Cefpodoxime proxetil, Ceftazidime, Ceftizoxime, Ceftriaxone, Cefepime, Azithromycin, Clarithromycin, Clindamycin, Dirithromycin, Erythromycin, Lincomycin, Troleandomycin, Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Perfloxacin, Imipenem-Cilastatin, Meropenem, Aztreonam, Amikacin, Gentamicin, Kanamycin, Neomycin, Netilmicin, Streptomycin, Tobramycin, Paromomycin, Teicoplanin, Vancomycin, Demeclocycline, Doxycycline, Methacycline, Minocycline, Oxytetracycline, Tetracycline, Chlortetracycline, Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Rifampin, Rifabutin, Rifampin, Rifapentine, Linezolid, Quinopristin Dalfopristin, Bacitracin, Chloramphenicol, Fosfomycin, Isoniazid, Methenamine, Metronidazol, Mupirocin, Nitrofurantoin, Nitrofurazone, Novobiocin, Polymyxin, Spectinomycin, Trimethoprim, Colistin, Cycloserine, Capreomycin, Ethionamide, Pyrazinamide, Para-aminosalicyclic acid, and Erythromycin ethylsuccinate.

14. The method of claim 13, wherein the antibiotic is tobramycin.

15. The method of claim 1, further comprising inhibiting or reducing biofilm formation by the bacteria via the administering of the therapeutically effective amount of ajoene formula (I).

16. The method of claim 1, further comprising administering the therapeutically effective amount of ajoene formula (I) in a pharmaceutical composition including at least 95% ajoene formula (I) with an E:Z isomer ratio of 1:2-1:6.

17. A method for inhibiting virulence of a bacteria in a mammal in need thereof, comprising:
a) selecting a mammal having an infection caused by a biofilm forming bacteria, wherein the bacteria is *Pseudomonas aeruginosa*; and
b) administering to the selected mammal a therapeutically effective amount of a garlic extract purified to 95% to 99.5% ajoene formula (I):

18. The method of claim 17, wherein the garlic extract includes 0.5% to 5% garlic extract components other than ajoene formula (I).